United States Patent [19]
Versluys et al.

[11] Patent Number: 5,567,387
[45] Date of Patent: Oct. 22, 1996

[54] CUVETTE CONVEYOR AND SENSOR

[75] Inventors: Richard J. Versluys, Spencerport; J. Daniel Riall, Pittsford, both of N.Y.

[73] Assignee: Johnson & Johnson Clinical Diagnostics, Inc., Rochester, N.Y.

[21] Appl. No.: 335,429

[22] Filed: Nov. 7, 1994

[51] Int. Cl.⁶ .................................................. G01N 21/13
[52] U.S. Cl. .......................... 422/67; 422/105; 422/107; 436/48
[58] Field of Search ................... 436/48, 50, 47, 436/54; 422/67, 105, 107

[56] References Cited

U.S. PATENT DOCUMENTS

| | | |
|---|---|---|
| 4,099,920 | 7/1978 | Heiss ........................................ 422/52 |
| 5,244,633 | 9/1993 | Jakubowicz et al. . |
| 5,266,272 | 11/1993 | Grinen et al. ......................... 422/102 |
| 5,271,896 | 12/1993 | Jakubowicz et al. . |
| 5,314,825 | 5/1994 | Weyrauch et al. ..................... 456/43 |
| 5,332,549 | 7/1994 | MacIndoe ............................... 436/48 |

*Primary Examiner*—Lyle A. Alexander
*Attorney, Agent, or Firm*—Dana M. Schmidt

[57] ABSTRACT

A conveyor and a method of providing a reaction cuvette using a conveyor, wherein a sensor is included to sense whether more than one cuvette is being conveyed. Because the cuvettes are received from a stack, one at a time, the sensor determines if two stacked cuvettes are present on the conveyor instead of one, by sensing the presence or absence of a cuvette projecting above the top of the desired cuvette.

6 Claims, 3 Drawing Sheets

CUVETTE CONVEYOR AND SENSOR

FIELD OF INVENTION

The invention concerns a conveyor of cuvettes, from a source to an incubator, and specifically, one which provides for the sensing of whether more than one cuvette is being so conveyed.

BACKGROUND OF THE INVENTION

It is known to drop cup-shaped cuvettes from a source, e.g., a stack, onto a conveyor of some kind, as shown in, e.g., U.S. Pat. Nos. 5,271,896 (FIGS. 4–8) and 5,244,633. However, it is important when this is done that only one cuvette be dispensed at a time. Prior to this invention, there has been a need for apparatus which advises specifically that there is more than one cuvette sitting at one station in the conveyor.

SUMMARY OF THE INVENTION

We have devised apparatus which satisfies the aforementioned need.

More specifically, there is provided in accordance with one aspect of the invention, a chemical analyzer comprising a conveyor for conveying a selected reaction cuvette from a cuvette dispensing station of the analyzer to a processing station for a dispensed cuvette, the conveyor including means for holding a cuvette in, and releasing a cuvette from, the conveyor. The analyzer is improved in that it further includes a sensor for sensing whether the number of cuvettes dispensed onto the conveyor is more than just one, by sensing the presence or absence of a cuvette projecting above the top of the selected cuvette.

In accordance with another aspect of the invention, there is provided such an analyzer wherein the improvement resides in a sensor for sensing whether the number of cuvettes dispensed is zero, by sensing the unobstruction of a beam of energy passed above the top of the conveyor.

In accordance with another aspect of the invention, there is provided a method of providing a reaction cuvette in an analyzer for a wet assay within the cuvette, comprising the steps of a) providing a source of reaction cuvettes within the analyzer, b) removing a cuvette from the source and onto a conveyor, c) conveying the removed cuvette to another portion of the analyzer by moving the conveyor, and d) in conjunction with step c), sensing whether or not only one cuvette has been removed onto the conveyor by step b).

Thus, it is an advantageous feature of the invention that an analyzer will automatically detect an accidental dispensing of more than one cuvette at a time onto the conveyor and take appropriate action.

It is a related advantageous feature of this invention that such detection can be done while the incubator is moving from the source of cuvettes to the rest of the analyzer, rather than stopping to perform this function at a separate station.

Other advantageous features will become apparent upon reference to the following "Detailed Description", when read in light of the attached drawings.

DESCRIPTION OF THE PREFERRED EMBODIMENTS

The invention is described with regard to the preferred embodiments, which convey a reaction cuvette of a preferred type for processing in a wet assay analyzer of a preferred type, for immunoassays, wherein cuvettes are dropped out of the conveyor and sensed by a light beam. In addition, the invention is useful regardless of a) the type of reaction cuvette being use, b) the type of wet assay analyzer being used, c) the type of assay performed in the cuvette, d) whether or not cuvettes are released from the conveyor by dropping them, and e) regardless of the type of energy beam used for sensing.

Figure 1:
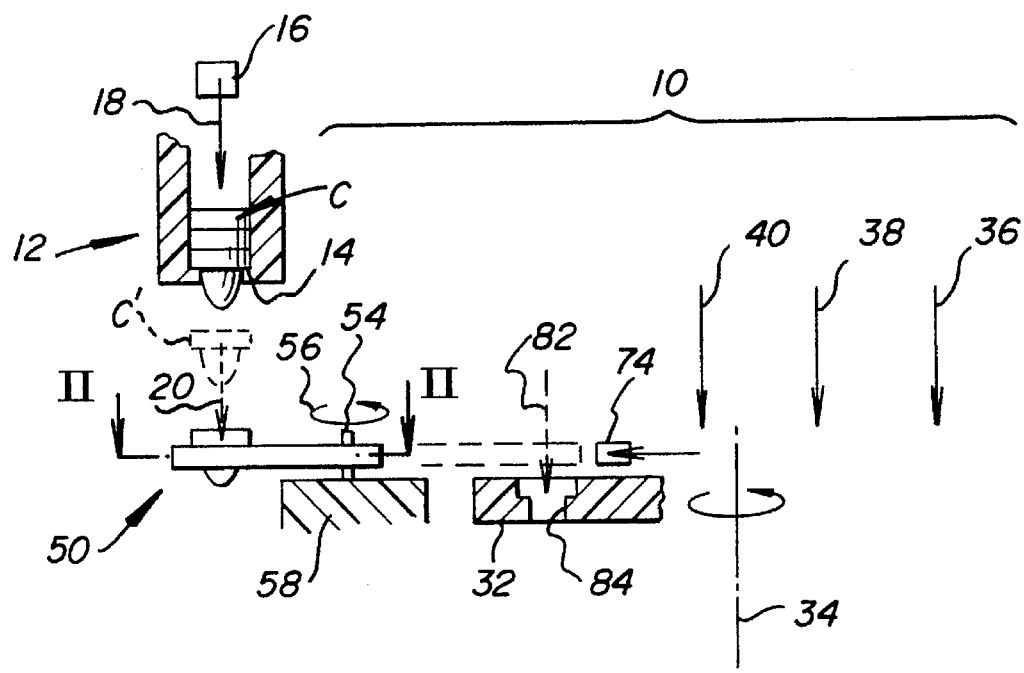
FIG. 1 is a fragmentary, partially schematic, elevational view in section of an analyzer constructed with a conveyor to transport a cuvette away from the stacked source of cuvettes.

Thus, the preferred cuvettes C, FIG. 1, are those described in U.S. Pat. No. 5,244,633, along with the preferred wet assay analyzer 10, and even more specifically, as described in commonly owned U.S. Ser. No. 163,104 filed on Dec. 7, 1993 by R. F. Jakubowicz et al entitled "Reagent Cup Shape Allowing Stacking Without Dislodging Reagent". That is, such cuvettes provide for a wet immunoassay using antibodies attached to surfaces inside the cuvette. The details of the aforesaid U.S. Ser. No. 163,104 are hereby expressly herein incorporated by reference.

Preferably, cuvettes C, FIG. 1, are provided from a source 12 that holds the cuvettes in the form of a stack 14. The bottommost cuvette is dispensed or removed from the stack by a suitable plunger 16 which is pushed downward, arrow 18. Plural stacks (not shown) can be provided via a reagent pack, such as that shown in commonly-owned U.S. Ser. No. 086,408 filed on Jul. 1, 1993 by D. Tomasso entitled "Locked Bottle Holder". Any plunger mechanism is useful, for example, that taught in the aforesaid U.S. Pat. No. 5,271,896.

As a cuvette C' falls off the stack, shown in phantom, arrow 20, it is caught by a conveyor 50 of the invention, described more fully hereinafter. This conveyor transfers the cuvette to an incubator ring 32 that is rotated about an axis 34 to carry the cuvette through processing stations 36, 38 and 40. Station 36, for example, is the station at which patient sample is deposited, and stations 38 and 40 the ones at which reagents are added as needed. Washing and reading are done at still other stations (not shown), the latter preferably at a luminometer. Some of these latter stations are preferably reached by transferring the cuvette to a second concentric ring, not shown, as described in the aforesaid '633 patent.

Figure 2:
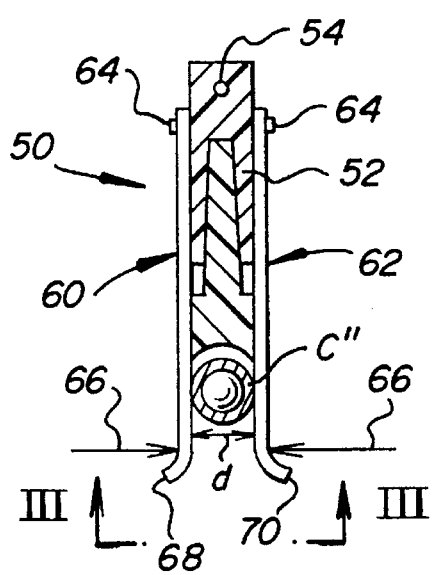
FIG. 2 is a section view taken generally along the line II—II of FIG. 1.
Figure 3:
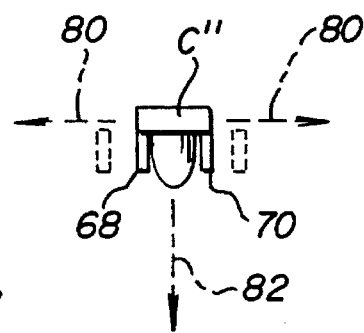
FIG. 3 is an end elevational view taken generally along the line III—III of FIG. 2.
Figure 4:
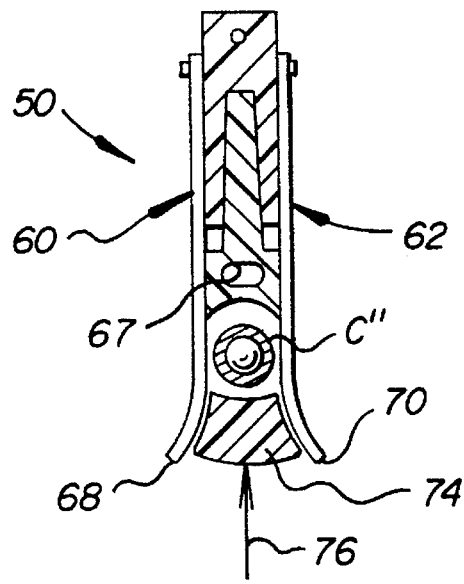
FIG. 4 is a section view similar to that of FIG. 2 but showing the release of a conveyed cuvette.

Conveyor 50, FIGS. 2–4, preferably comprises an arm 52 pivotally mounted at one end 54 to rotate, arrow 56, FIG. 1, about a fixed base 58. Arm 52, FIG. 2, which can comprise two pieces joined together as shown, includes a pair of spring jaws 60, 62 attached at ends 64 to arm 52 near end 54 of the latter. Arm 52 has a top surface 65, FIG. 1, and an aperture 67. These spring jaws are biased by this attachment to press inwardly, arrows 66. Thus they are normally spaced apart a distance "d" that is just sufficient to catch and hold a cuvette C''' therein, released from stack 14, between the jaws' free ends 68, 70 opposite to ends 64. See also FIG. 3.

To release cuvette C''' when arm 52 is pivoted to its phantom position above ring 32, FIG. 1, a camming member 74 is provided. Member 74 is pushed by a suitable mechanism, arrow 76, FIG. 4, to pass between ends 68, 70 of jaws 60 and 62. The increasing taper of member 74 is effective to spread apart ends 68, 70, arrows 80, FIG. 3, to thus release cuvette C''' which then falls, arrow 82, into an aperture 84 of ring 32, FIG. 1. See also FIG. 3 which shows the spread-apart ends in phantom.

Figure 5:
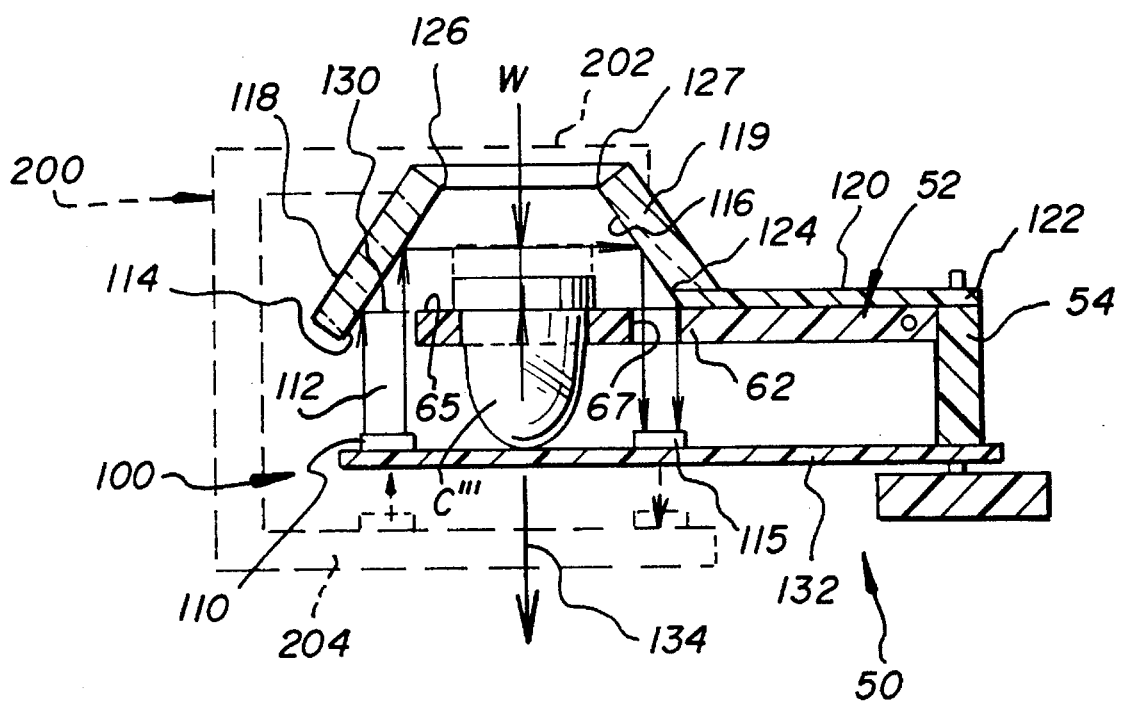
FIG. 5 is a fragmentary elevational view of the sensor and sensing method of the invention.

In accordance with the invention, in order to sense whether or not more than one cuvette has been dispensed or released onto conveyor 50, a sensor 100 is provided, FIG. 5, either as part of the conveyor as shown, or as a separate station 200 in the analyzer, shown in phantom. In either case sensor 100 comprises a source 110 of electromagnetic radiation, e.g. an LED that emits an infrared light beam 112, at least one mirror 114, and a detector such as a photodiode 115 for such electromagnetic radiation. A pair of reflecting surfaces, e.g., mirrors 114, 116, is preferably used, each at a 45° angle to the light beam, mounted on portions 118 and 119, respectively, of an arm 120 that extends from an end 122 attached to pivoted end 54 of arm 52, arm 120 being angled upward at 124 to provide a first support (for mirror 116) and downward at 126 to provide a second support (for mirror 114). An aperture 127 in the arm allows a cuvette C to fall through to arm 52, to rest on jaws 60,62. (Source 110 and detector 115 are preferably supported on an arm 132 that parallels arm 52, with an aperture therein, not shown, that easily allows cuvette C''' to fall through, arrow 134, when the spring jaws 60, 62 release.) A conventional microprocessor, not shown, is used to interpret and process the signals from detector 115.

The operation of the sensor is preferably one that detects whether one cuvette C''', FIG. 5, has been received, or some other number, namely zero or more than one. This is done by the projection across the top surface 65 of arm 52, of a broad beam 112 the width W of which encompasses both a single cuvette, shown in solid, or more than one caused by a second (or even a third) cuvette (in phantom) stacked on top of cuvette C'''. Detector 115 will then detect the entire beam, or a fraction of the beam, or essentially no beam. Those three conditions represent, respectively, zero cuvettes dispensed, only one dispensed, and more than one dispensed. The strength of the signal received is then converted by conventional software into a "go" or "no-go" signal to the analyzer, in which the "go" signal occurs only when only the fraction of the beam is detected.

If the "no-go" signal is generated, then the signal is examined to see if the beam received was full strength or essentially zero strength. If the former is the case, another cuvette is dispensed. If the latter is the case, the unacceptable stack of more than one cuvettes on conveyor 50 is dumped at an appropriate location, and arm 52 is returned for a repeat of the cuvette dispensing step until it is detected that only one cuvette is received.

Alternatively (not shown), beam 112 can be narrowed in width to detect only that a cuvette has or has not been dispensed (the beam is narrowed to be obstructed by only the first cuvette), or that only a stack (more than one cuvette) has not or has been dispensed (the narrow beam passes above a single dispensed-and-received cuvette). It will be appreciated, however, that the better approach is to use the wide beam W to detect all three conditions.

In the above embodiment, sensor 100 moves continuously with conveyor 50, so that the sensing of more than one cuvette being in place can be done any time, even while the conveyor is conveying the cuvette.

Alternatively, shown in phantom, portions 118, 119 of arm 120 mounting mirrors 114 and 116 can be, instead, projections extending from a fixed station 200 having a top bar 202 to which portions 118, 119 are attached at the appropriate angles. In such a case, arms 120 & 132 are omitted and instead source 110 and detector 116 are mounted, shown in phantom, on bottom bar 204 of station 200. Sensing then is done by rotating conveyor 50 so as to pass through station 200 on the way to carrying a cuvette to ring 32.

Figure 6:
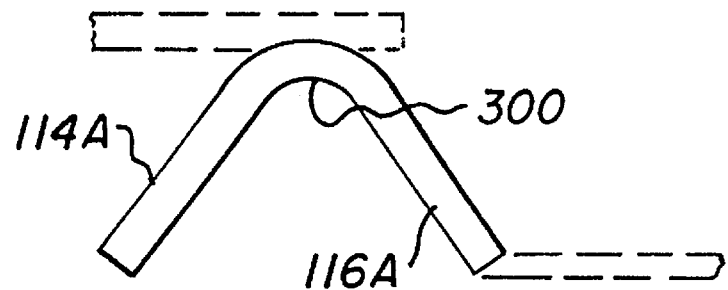
FIGS. 6 and 7 are fragmentary views similar to that of FIG. 5, but of alternate embodiments.

Yet another alternative is to use a single mirror in place of the two. This is done in the embodiment of FIG. 6 in that the mirror surface is a single mirror having two flat portions 114A and 116A, joined together by a curved portion 300. The mounting of the mirror is as shown in phantom, depending on whether the mirror is carried by the conveyor or is fixed in place.

Figure 7:
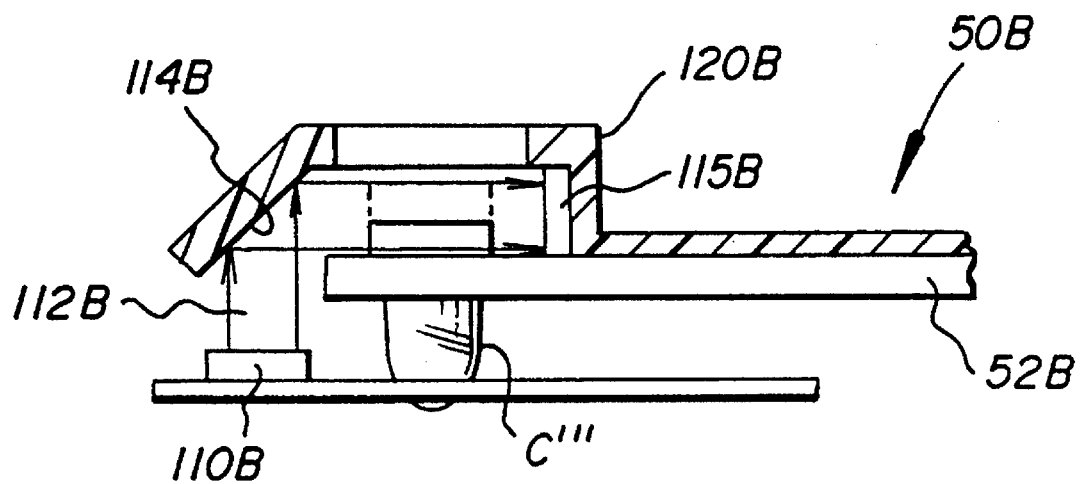

In yet another alternative embodiment, FIG. 7, a single mirror with only one flat portion is used. Parts similar to those previously described bear the same reference numeral to which a distinguishing "B" is appended. Thus, conveyor 50B has an arm 52B to receive a cuvette such as C''', and an energy source 110B is used with detector 115B to detect zero, one, or more than one cuvette, as described above. However, only mirror 114B is mounted on arm 120B, and in place of the reflecting surface 116 used in the other embodiments, detector 115B is mounted.

The invention has been described in detail with particular reference to preferred embodiments thereof, but it will be understood that variations and modifications can be effected within the spirit and scope of the invention. For example, although other features can be added besides those described, it is also useful free of any other features. That is, it can consist of only the enumerated parts.

What is claimed is:

1. In a chemical analyzer comprising a conveyor for conveying a selected reaction cuvette from a cuvette dispensing station of the analyzer to a processing station, said conveyor including means for holding a cuvette in, and releasing a cuvette from, said conveyor, the improvement wherein said analyzer further includes a sensor for sensing whether the number of cuvettes dispensed onto said conveyor is more than just one, by sensing the presence or absence of a cuvette projecting above the top of said selected cuvette.

2. An analyzer as defined in claim 1, wherein said sensor is part of said conveyor.

3. An analyzer as defined in claim 1, wherein said sensor is not part of said conveyor, and further including means for moving said conveyor into a position adjacent said sensor sufficient to detect said second cuvette if present, and then out of said position.

4. An analyzer as defined in claim 1, wherein said sensor comprises a light source, a light detector, and at least one mirror operatively disposed to direct light from said source across the top of said selected cuvette and to said detector.

5. An analyzer as defined in claim 4, wherein said sensor is part of said conveyor.

6. An analyzer as defined in claim 4, wherein said sensor is not part of said conveyor, and further including means for moving said conveyor into a position adjacent said sensor sufficient to detect said second cuvette if present, and then out of said position.

* * * * *